United States Patent
Plaumann et al.

(10) Patent No.: US 9,913,699 B2
(45) Date of Patent: Mar. 13, 2018

(54) MIXING CAPSULE FOR PRODUCING A DENTAL PREPARATION

(71) Applicant: VOCO GmbH, Cuxhaven (DE)

(72) Inventors: Manfred Thomas Plaumann, Cuxhaven (DE); Andree Barg, Otterndorf (DE); Uwe Leiner, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 151 days.

(21) Appl. No.: 14/973,094

(22) Filed: Dec. 17, 2015

(65) Prior Publication Data

US 2016/0199166 A1 Jul. 14, 2016

(30) Foreign Application Priority Data

Jan. 14, 2015 (DE) .................. 10 2015 200 424

(51) Int. Cl.
| | |
|---|---|
| *A61C 19/00* | (2006.01) |
| *A61C 5/66* | (2017.01) |
| *B01F 15/02* | (2006.01) |
| *B05B 11/00* | (2006.01) |
| *B05B 11/02* | (2006.01) |

(Continued)

(52) U.S. Cl.
CPC ............... *A61C 5/66* (2017.02); *A61C 5/64* (2017.02); *A61C 19/005* (2013.01); *B01F 13/0022* (2013.01); *B01F 15/0212* (2013.01); *B01F 15/0223* (2013.01); *B01F 15/0237* (2013.01); *B05B 11/0081* (2013.01); *B05B 11/02* (2013.01)

(58) Field of Classification Search
CPC ...................................................... A61C 19/00

USPC ............................................... 366/176.3, 189
See application file for complete search history.

(56) References Cited

U.S. PATENT DOCUMENTS 3,353,918 A * 11/1967 Perrin .................. B01F 5/0685
 261/DIG. 26
3,907,106 A 9/1975 Purrmann et al.
(Continued)

FOREIGN PATENT DOCUMENTS

| EP | 0783872 | 7/1997 |
| EP | 1029513 | 8/2000 |

(Continued)

*Primary Examiner* — David Sorkin
(74) *Attorney, Agent, or Firm* — Duane Morris LLP; J. Rodman Steele, Jr.; Gregory M. Lefkowitz

(57) ABSTRACT

In order to develop mixing and application capsules known from the prior art, so that limitations regarding the dental preparations that can be obtained are overcome, a mixing capsule (22) for producing a dental preparation is proposed in which the mixing capsule (22) has: a capsule body (1) having a mixing chamber for receiving a mixing component and for mixing the dental preparation from the mixing component, a first fluid and a second fluid and having an outlet opening (4) for expelling the dental preparation, a first cavity for receiving the first fluid, a first piston body (2) which delimits the mixing chamber in the capsule body (1) and which has a first passageway for guiding the first fluid from the first cavity into the mixing chamber, a second cavity for receiving the second fluid and a second piston body (2) which delimits the mixing chamber in the capsule body (1) and which has a second passageway for guiding the second fluid from the second cavity into the mixing chamber.

12 Claims, 11 Drawing Sheets

(51) Int. Cl.
*B01F 13/00* (2006.01)
*A61C 5/64* (2017.01)

(56) References Cited

U.S. PATENT DOCUMENTS

| | | | |
|---|---|---|---|
| 4,889,732 | A | 12/1989 | Patterson et al. |
| 5,153,231 | A | 10/1992 | Bouquet et al. |
| 6,062,722 | A * | 5/2000 | Lake .................... B01F 5/0615 366/130 |
| 8,308,340 | B2 * | 11/2012 | Ferrante ........... A61B 17/00491 222/137 |
| 2002/0087122 | A1 | 7/2002 | Sogaro |
| 2004/0167617 | A1 * | 8/2004 | Voellmicke ........... A61F 2/4644 623/1.23 |
| 2009/0177179 | A1 | 7/2009 | Engelbrecht |
| 2010/0261139 | A1 | 10/2010 | Leiner et al. |
| 2012/0258422 | A1 | 10/2012 | Leiner et al. |

FOREIGN PATENT DOCUMENTS

| | | |
|---|---|---|
| GB | 1107894 | 3/1968 |
| JP | 2012130797 | 7/2012 |

* cited by examiner

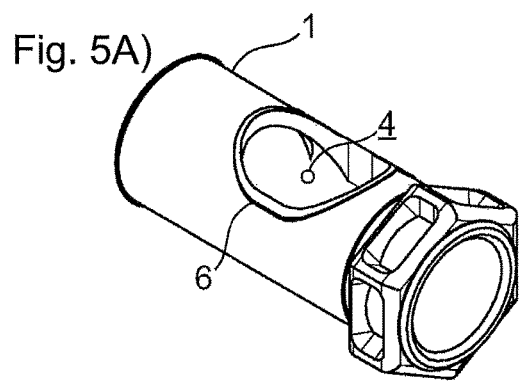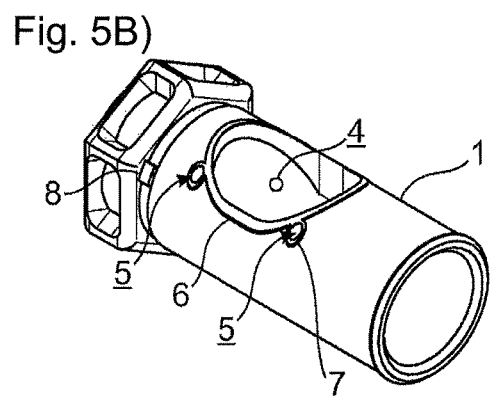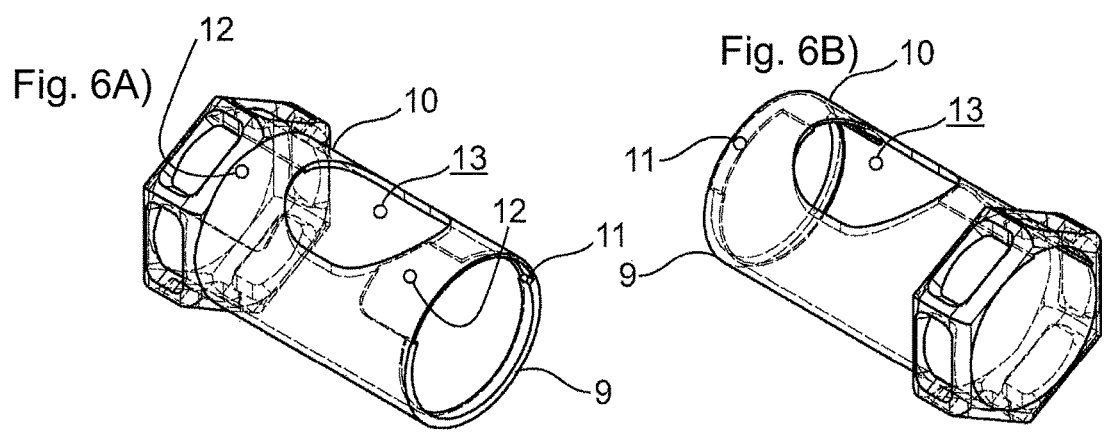

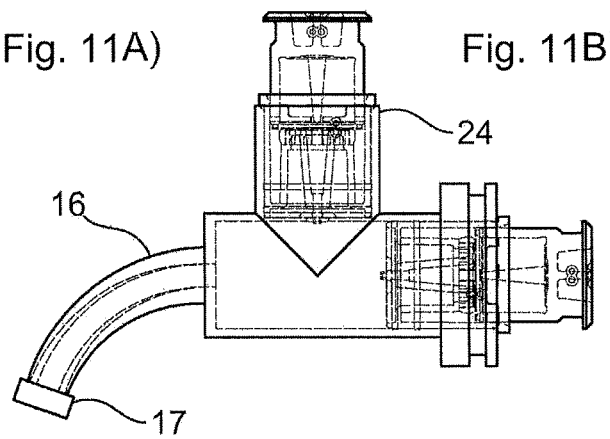
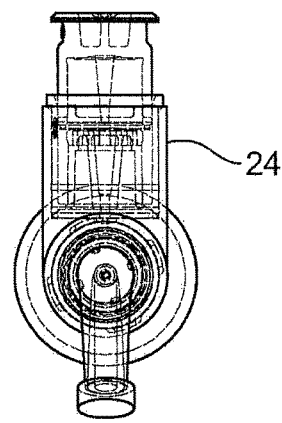
Fig. 11A) Fig. 11B)
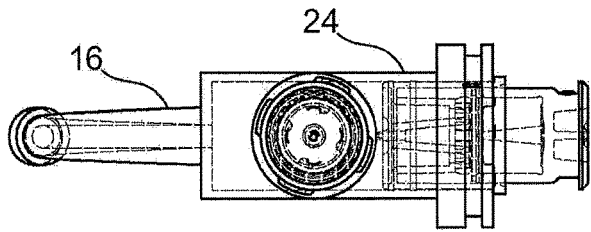
Fig. 11C)
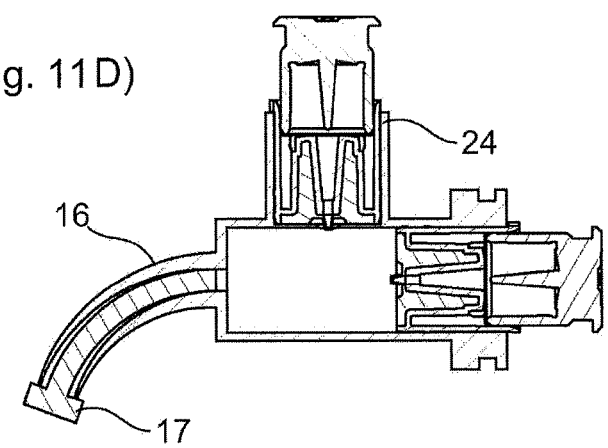
Fig. 11D)

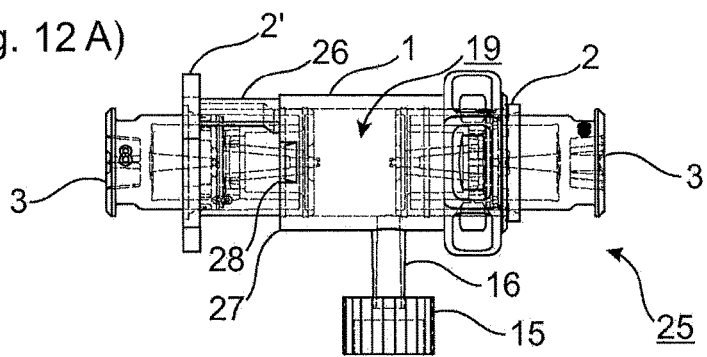
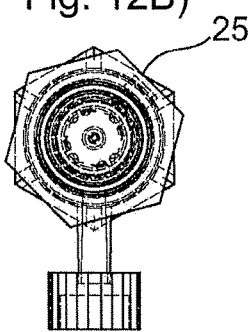
Fig. 12 A) Fig. 12B)
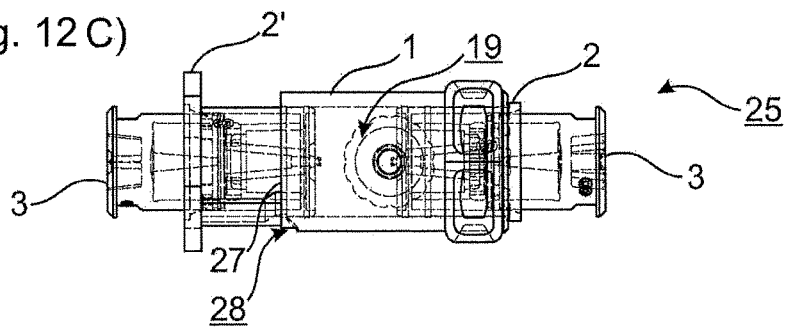
Fig. 12 C)
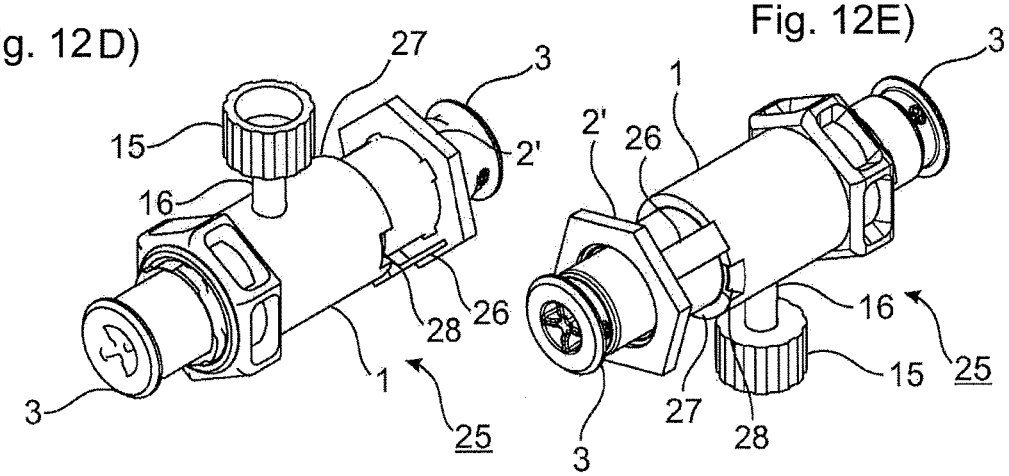
Fig. 12 D) Fig. 12E)

MIXING CAPSULE FOR PRODUCING A DENTAL PREPARATION

CROSS REFERENCE TO RELATED APPLICATIONS

This application claims priority to German Patent Application No. 102015200424.4, filed Jan. 14, 2015, the entire contents of which are incorporated herein by reference.

BACKGROUND OF THE INVENTION

The present invention relates to a mixing capsule for producing a dental preparation, the dental preparation being mixed from different components in a mixing chamber of the mixing capsule, which is securely positioned inside the mixing capsule until mixing.

The expression "dental preparation" refers here to multi-component materials such as adhesives, filling materials, fixing materials in general (fixing cements in particular) and glass ionomers, but not to amalgams or amalgam mixtures. The invention is firstly aimed at providing a mixing capsule, but one which, in addition to its function as a "mixing capsule", can also be used in certain circumstances as an application capsule.

Mixing capsules which can also be used as application capsules are known, for example, from EP 0 783 872 A2, EP 1 029 513 A2, EP 2 238 942 A2 and EP 2 510 897 A2.

A common feature of these mixing capsules is that they are each adapted to mix two components, which means that, due to the limited range of possible combinations this entails, there are limitations regarding the achievable properties of the mixed dental preparations.

A disposable packaging system which also allows three or even more components to be mixed is described in DE 10 2006 015 238 A1. In the disposable packaging system described therein, however, mixing is done in such a way, due to the technical principle on which the system is based, that a first and a second component are firstly mixed with each other, before the combination of first and second component is then added to the third component. Mixing according to DE 10 2006 015 238 A1 is a cascading, step-by-step mixing process in which several mixtures each composed of two mixing components (pure components or mixtures of components) are brought together.

However, such serial mixing of components does not appear to be possible with the mixing and application capsules known from EP 0 783 872 A2, EP 1 029 513 A2, EP 2 238 942 A2 or EP 2 510 897 A2.

One wish underlying the present invention is to provide a mixing capsule which still allows advantages such as those known and described for the mixing and application capsules known from EP 0 783 872 A2, EP 1 029 513 A2, EP 2 238 942 A2 and EP 2 510 897 A2, but which also overcomes the limitations regarding the dental preparations that can be obtained.

BRIEF SUMMARY OF THE INVENTION

A mixing capsule for producing a dental preparation is therefore proposed, wherein the mixing capsule comprises: a capsule body having a mixing chamber for receiving a mixing component and for mixing the dental preparation from the mixing component, a first fluid and a second fluid and having an outlet opening for expelling the dental preparation, a first cavity for receiving the first fluid, a first piston body which delimits the mixing chamber in the capsule body and which has a first passageway for guiding the first fluid from the first cavity into the mixing chamber, a second cavity for receiving the second fluid and a second piston body which delimits the mixing chamber in the capsule body and which has a second passageway for guiding the second fluid from the second cavity into the mixing chamber.

The expression "fluid" should be understood here in such a way that liquids, gases and also pastes are also included.

One realisation on which the invention is based is that a structure, in which the piston bodies with the respective cavities and passages for guiding the respective fluid from the cavity to the mixing chamber each delimit the mixing chamber as well, allows a plurality of such piston bodies to be provided parallel to each other, so that not just one fluid but a plurality of fluids can be introduced into the mixing chamber independently of each other.

In one embodiment of the invention, the mixing capsule has a sleeve which encloses the capsule body at least partially and which is to be disposed in at least a first and a second position relative to the capsule body, the sleeve closing the outlet opening in the first position and exposing the outlet opening in the second position, so that the dental preparation can be expelled through the outlet opening.

The sleeve acts specifically as a closure means for the outlet opening, and the arrangement in which the sleeve encloses the capsule body in at least one portion thereof and/or over at least part of its circumference, allows a simple construction and thus low costs, without significantly compromising the closure characteristics as a result.

In a development of the embodiment, the sleeve has an opening, and the sleeve opening and the outlet opening can be brought into alignment with each other in the second position by turning and/or sliding the sleeve and the capsule body relative to each other, so that the dental preparation can be expelled through the outlet opening and the sleeve opening, and can be separated from each other in the first position so that the sleeve closes the outlet opening.

It is advantageous that the sleeve itself has an opening (for example in the form of a hole, a recess, a slot or the like) which matches the outlet opening of the capsule body to such an extent that the two openings can be brought into alignment with other with a respective relative movement (e.g. coaxial rotation or lateral movement along a longitudinal axis), so that it is possible to access the mixing chamber through the sleeve and the outlet opening, or to remove material from the mixing chamber in the reverse direction.

In one variant of the embodiment, the capsule body has a cylindrical outer shape in at least one portion thereof, the outlet opening being located in said portion, the sleeve enclosing the capsule body at least partially in at least a part of said portion and being configured so that the sleeve and the capsule body can be turned relative to each other.

The cylindrical shape allows the sleeve and the capsule body to be turned relative to each other in a reliable manner yet also sealingly, by simple means and even when the materials are not deformable or only minimally deformable.

If at least one of the elements involved, i.e., the sleeve and/or the capsule body, is adapted for preferably resilient deformation, then it also possible to depart from the cylindrical shape if the deformability allows the outlet opening to remain sealed during turning. For example, if a sleeve has elastic edge regions at least, which hug the outer shape of the capsule body, it is also possible for the capsule body to be provided with an oval cross-section (or other cross-sectional shapes as well, provided that the radii of convex curvature do not prevent such hugging, and that there are no surface areas that are convex).

The closing and opening of the outlet opening by turning and/or sliding the sleeve can be advantageously provided in such a way that the sleeve remains on the capsule body, so that, in use, the sleeve and the capsule body are not separate elements that have to be disposed of separately from each other. For example, if the outlet opening is exposed simply by turning the sleeve relative to the capsule body, the operator does not need to set a removed sleeve to the side, which means that handling is simplified on the whole.

In another variant of the embodiment, the sleeve opening leads to an application means for the sleeve, in particular to a cannula.

The sleeve opening may be provided with a cannula, for example, so that the sleeve not only acts as a closure means for the outlet opening, but also serves as a support for an application or for some other way of removing the dental preparation.

In this respect, at least one of the piston bodies may be displaceable inside the capsule body, such that pressing the respective piston body into the capsule body causes the mixing chamber to be reduced in size, thus allowing the dental preparation to be expelled out of the mixing chamber and through the application means. Alternatively, or in addition thereto, a separate piston acting on the mixing chamber may also be provided, or some other suitable way of configuring the mixing chamber.

In another development, the first piston body is adapted to close the outlet opening, the sleeve being separated in the second position from the capsule body and the sleeve being adapted to entrain the first piston body in order to expose the outlet opening on separation of the sleeve from the capsule body.

The sleeve can be pulled off the capsule body, the first piston body also being removed from the capsule body in the process in order to expose the interior of the mixing chamber, similarly to a beaker. The sleeve and the first piston body may be separate elements which are coupled to each other by a form fit, for example. However, the sleeve and the first piston body may also be integrally formed as one piece, or be intimately connected to each other in some other manner.

It is also possible to remove the second piston body as well from the capsule body, and if the sleeve is in two parts, then the second part of the sleeve can cause the second piston body to be entrained here as well.

In one embodiment of the invention, the piston body and/or the sleeve have one or more detent means for snap-locking the piston body and the sleeve together in the first, the second and/or in a third position.

A detent mechanism allows controlled positioning, so that, during use, an acoustic or haptic signal produced by the detent mechanism indicates to the user that a particular position has been reached. The detent mechanism also allows restriction of movement between the sleeve and the capsule body.

In another embodiment, the first and the second piston body are arranged opposite one another and the mixing chamber is located between the first and the second piston body.

By pressing together opposite pistons which interact with the piston body, the fluids can be introduced into the mixing chamber. The pistons or piston bodies are arranged not only opposite each other, but are preferably also arranged coaxially with each other.

In yet another embodiment, the first piston body and/or the second piston body are displaceable inside the capsule body.

When displaceable piston bodies are provided, it is possible by exerting pressure on the respective piston body to exert a pressure on the dental preparation in the mixing chamber, for example to expel the dental preparation out of the mixing chamber and through the outlet opening.

In one variant of this embodiment, the mixing capsule has a blocking means with which the piston body can be blocked or prevented from moving. By means of the blocking means, this displaceability can be permitted by the user in a controlled manner, as a result of which the ease of handling can be enhanced. The blocking means preferably includes interacting elements which can adopt a first blocking position or a second releasing position. It is particularly preferred that a transition between the blocking position and the releasing position includes turning the piston body and the capsule body relative to one another.

In one embodiment of the invention, the first piston body can be displaced up to a maximum depth of penetration into the capsule body, the first piston body adjoining the outlet opening at its maximum depth of penetration.

If the first piston body is moved to its maximum depth of penetration, the outlet opening is located at an end portion of the mixing chamber that has been reduced in size, which can be advantageous when emptying, for example.

In one embodiment of the invention, the outlet opening is provided in the first and/or the second piston body and is closed by a removable closure means.

It is not necessarily the case that the outlet opening is provided in a wall of the mixing chamber that is separate from the piston bodies. It is equally possible that expulsion is through one of the piston bodies themselves, in particular through an initially plugged through hole provided in the longitudinal direction of the piston body.

In another embodiment of the invention, the mixing capsule has a sleeve which encloses the capsule body at least partially and which is to be disposed in at least a third and a fourth position relative to the capsule body, the sleeve having a cavity for receiving an admixing component, the sleeve being arranged in the third position in such a way that the cavity is in communication with the mixing chamber so that admixing components can enter the mixing chamber, and the collar is arranged in the fourth position in such a way that the cavity is shut off from the mixing chamber 19) and from surroundings of the mixing capsule.

In addition to the sleeve opening (if provided), the sleeve can also have a chamber (or indeed several chambers) for receiving at least one powder, or similar. In one position, the outlet opening is closed by the sleeve, whereas in another position the outlet opening is exposed by the sleeve opening, and in a third position the powder or similar can get into the mixing chamber from the chamber.

BRIEF DESCRIPTION OF THE SEVERAL VIEWS OF THE DRAWINGS

The invention shall now be described in greater detail with reference to some embodiments and to the enclosed Figures, in which

FIG. 5A shows first perspective view of the capsule body of the mixing capsule according to the first embodiment.

FIG. 5B shows second perspective view of the capsule body of the mixing capsule according to the first embodiment.

FIG. 6A shows first perspective grid view of a sleeve of the mixing capsule according to the first embodiment.

FIG. 6B shows second perspective grid view of a sleeve of the mixing capsule according to the first embodiment.

FIG. 11A shows a side view of a mixing capsule according to a third embodiment of the invention.

FIG. 11B shows a right side view of the mixing capsule according to the third embodiment of the invention.

FIG. 11C shows a top side view of the mixing capsule according to the third embodiment of the invention.

FIG. 11D shows a cross-section view of the mixing capsule according to a third embodiment of the invention.

FIG. 12A shows a side view of the mixing capsule according to a fourth embodiment of the invention, in an initial state.

FIG. 12B shows a right side view of the mixing capsule according to a fourth embodiment of the invention, in an initial state.

FIG. 12C shows a top side view of the mixing capsule according to a fourth embodiment of the invention, in an initial state.

FIG. 12D shows a first perspective view of a mixing capsule according to a fourth embodiment of the invention, in an initial state.

FIG. 12E shows a second perspective view of a mixing capsule according to a fourth embodiment of the invention, in an initial state.

DETAILED DESCRIPTION OF THE INVENTION

Figure 1:
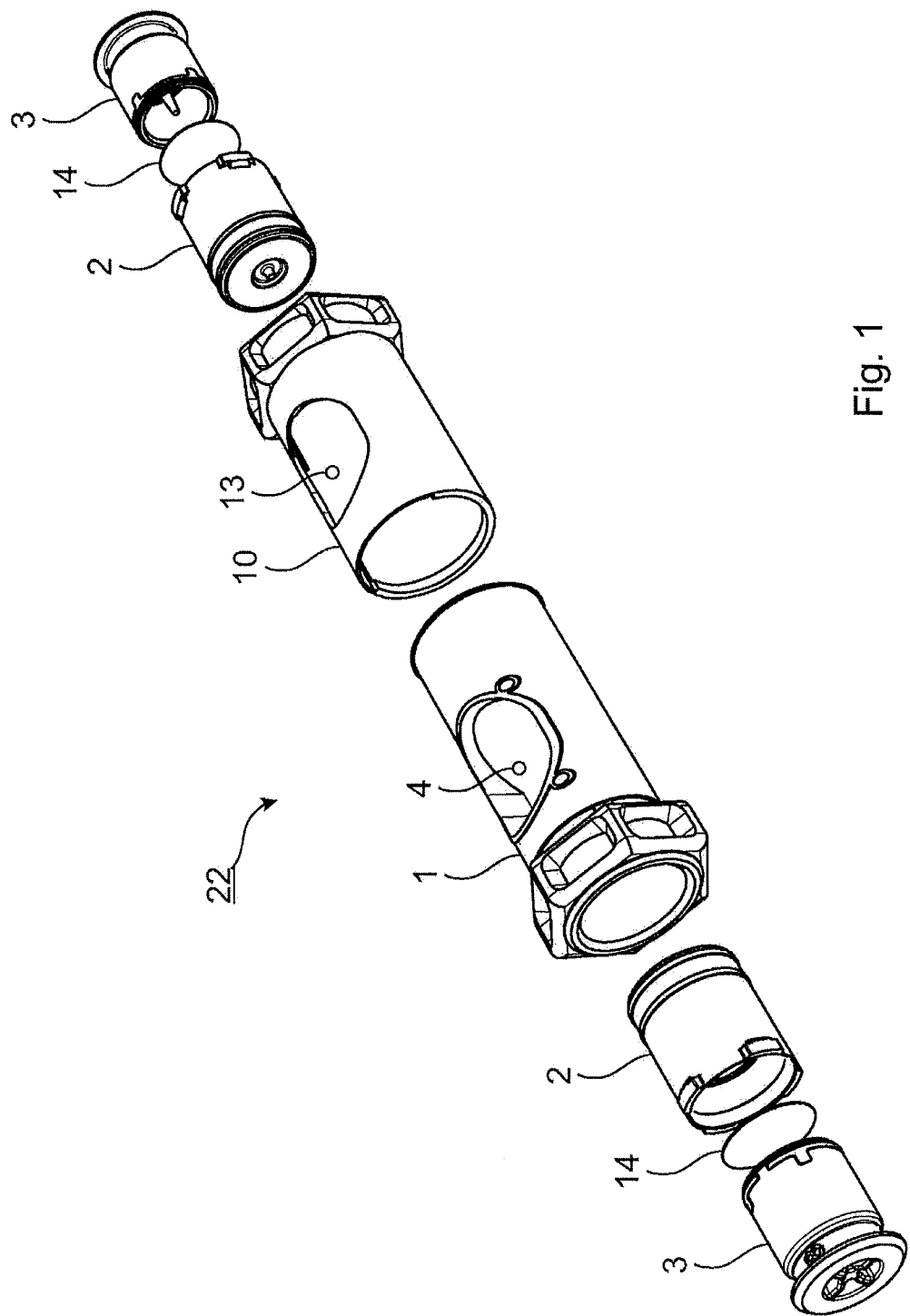
FIG. 1 shows an exploded view of a first embodiment of a mixing capsule according to the invention.

FIG. 1 shows an exploded view of a first embodiment of a mixing capsule 22 according to the invention.

Mixing capsule 22 comprises a capsule body 10, a sleeve 11, two piston bodies 2 each having associated pistons 3, which for their part are each provided with a film 14.

Capsule body 1 has a substantially cylindrical shape, with sleeve 10 substantially enclosing capsule body 1 in operation. Piston bodies 2 are inserted into the initially open ends of the capsule body, a piston 3 sealed with a film 14 on the side facing piston body 2 being provided in each piston body.

FIGS. 2A through 2F shows views and cross-sections of the mixing capsule 22 according to the first embodiment.

Figure 2:
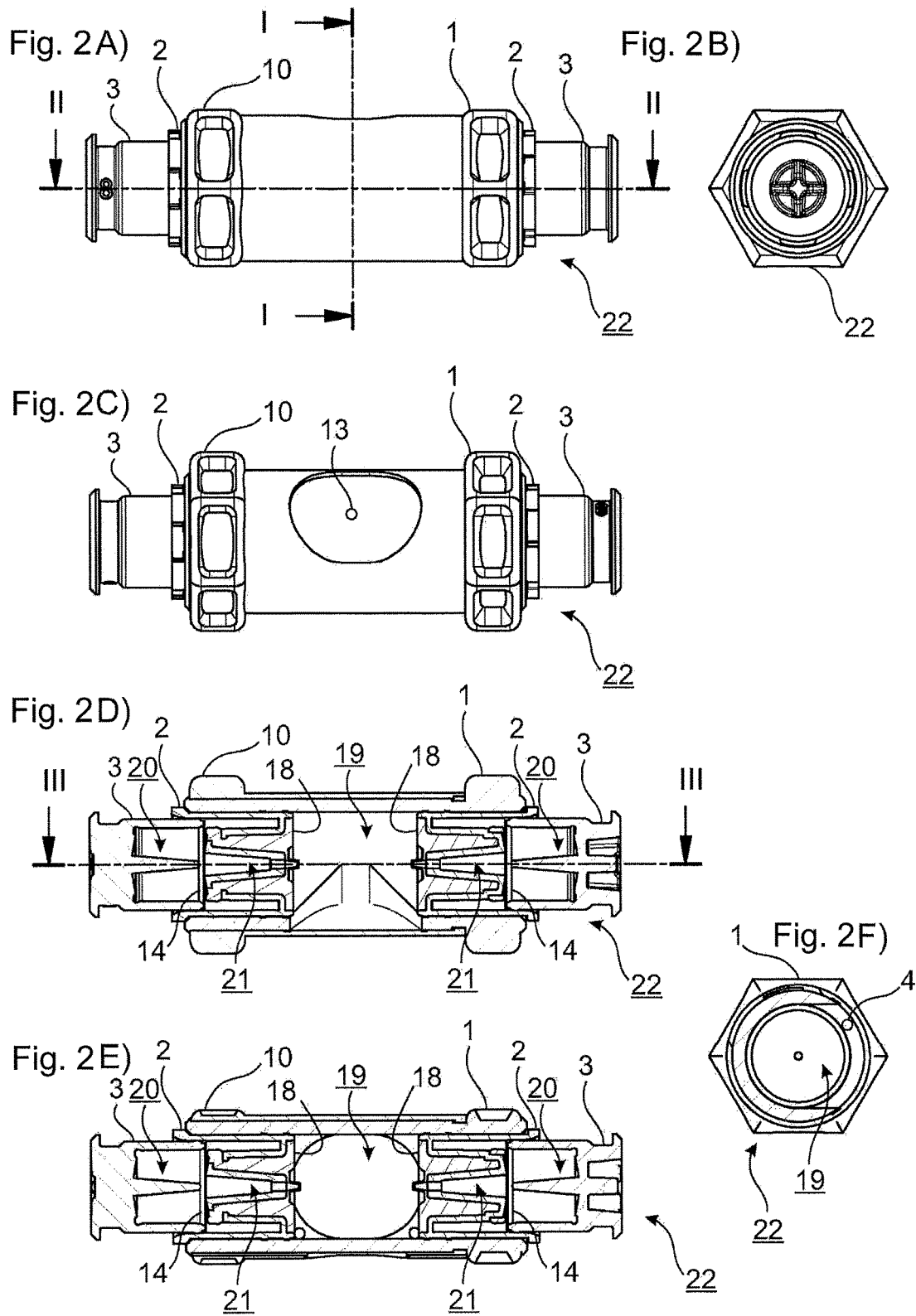
FIG. 2A shows a view of the mixing capsule with the sleeve pushed onto capsule body.
FIG. 2B shows a view of the mixing capsule along its longitudinal axis.
FIG. 2C shows a view of the mixing capsule as rotated about its longitudinal axis in order to show the sleeve opening.
FIG. 2D shows a view of the piston bodies inserted into the capsule body as indicated in the sectional plane II of FIG. 2A.
FIG. 2E shows a view of the mixing capsule as indicated in cross-sectional plane III of FIG. 2D.
FIG. 2F shows a sectional view of plane II of FIG. 2D.

FIG. 2A shows a side view of mixing capsule 22 with sleeve 10 pushed onto capsule body 1. Piston bodies 2 have each been inserted into capsule body 1, and pistons 3 have been inserted slightly into piston bodies 2.

In FIG. 2A, two sectional planes are marked, sectional plane I corresponding to the view shown in FIG. 2F and sectional plane II being illustrated in FIG. 2D.

FIG. 2B shows a view of mixing capsule 22 along its longitudinal axis.

FIG. 2C shows a view of mixing capsule 22 that is basically the same as the view shown in FIG. 1A, but in which, in contrast to the latter, the mixing capsule is rotated about its longitudinal axis so that sleeve opening 13 of sleeve 10 can be seen in the view shown in FIG. 2C.

As can be seen in FIG. 2D, the piston bodies inserted into capsule body 1 delimit a mixing chamber in the capsule body, said mixing chamber thus being delimited by the side wall of capsule body 1 and the sides 18 of piston body 2 facing mixing chamber 19.

There is a cavity 20 in each of pistons 3, containing a fluid component (not shown) of the partial preparation to be mixed.

Said cavity 20 is closed initially by film 14, so that the respective component can be securely stored in piston 3. Piston bodies 2 each have a passageway 21 through which the components can get from cavity 20, when the latter is opened, into mixing chamber 19.

FIG. 2E shows a different cross-section through mixing capsule 22, as indicated by sectional plane III in FIG. 2D.

Figure 3:
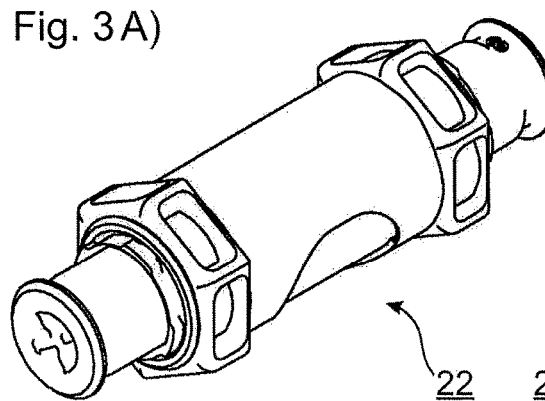
FIG. 3A shows a view of the mixing capsule before being used wherein the sleeve opening and the outlet opening of the capsule body are brought into ling with each other to expose the mixing chamber to the outside world.
FIG. 3B shows a view of the mixing capsule in which the pistons are each inserted fully into the piston bodies so that the first and second fluid have flowed through passageways into the mixing chamber.
Figure 3:
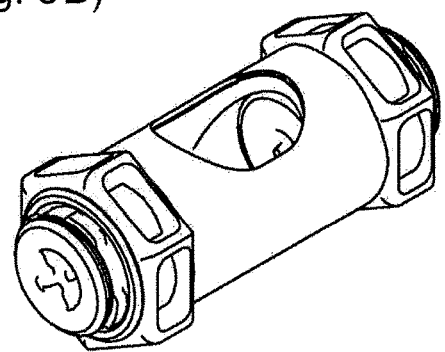

FIGS. 3A and 3B shows perspective views of mixing capsule 22 according to the first embodiment.

In the view shown in FIG. 3A, mixing capsule 22 is in a form it can have before being used. Pistons 3 are already inserted into piston bodies 2, but only so far that film 14 is still intact.

FIG. 3B shows the mixing capsule in a state in which pistons 3 are each inserted fully into piston bodies 2, so that the first and second fluid, which were initially held in said pistons 3 or in cavities 20 thereof, have flowed through passageways 21 into mixing chamber 19, where they are mixed with a mixing component provided there. In comparison with FIG. 3A, the sleeve has been turned so that the sleeve opening and the outlet opening of the capsule body are brought into line with each other to expose the mixing chamber to the outside world.

As already described in the foregoing, the mixing capsule comprises an inner, cylindrical capsule body 1 and an outer sleeve 10. Both have a respective hole (outlet opening 4 and sleeve opening 13), which are aligned with each other by rotation, thus causing the mixing capsule as a whole to be opened. The two ends of capsule body 1 are each closed by a piston body 2 that is securely attached in capsule body 1 in this embodiment, even though piston body 2 is depicted first of all as a separate component. However, the piston body may also be formed as an integral part of the capsule body or may also be kept as a part which is separate from and displaceable in relation to the capsule body. The purpose of said piston bodies 2 is to delimit mixing chamber 19 inside capsule body 1 and simultaneously to allow liquid and/or pasty components to be supplied. A further piston 3 is mounted on each piston body 2. Said piston 3 contain the aforementioned liquid and/or pasty masses, which get to the mixing chamber by being moved in the direction of mixing chamber 19 through piston bodies 2 by the exertion of pressure on pistons 3. Pistons 3 may be sealed by a film 14, which is then torn by piston body 2 when pressure is exerted on the latter.

The finished mixing system in this embodiment includes at least two liquid to pasty (A1 and A2) components and a solid, stuffable, liquid or pasty component (C1). Components A1 and A2 are in pistons 3, and at least one component C1 is inside mixing chamber 19 of capsule 22. When pistons 3 are activated, all the components are present inside mixing chamber 19 of capsule body 1. The components can now be either mixed with the aid of a commercially available capsule mixer, or manually stirred using a suitable implement (e.g. a spatula) when capsule 22 is open. Capsule 22 must previously be opened by turning outer sleeve 10. The ventilation slots provided in capsule 22 allow the overpressure produced by activation to be released.

After mixing and opening, application is carried out by likewise removing the preparation using a suitable implement.

Application through a discharge cannula attached to the capsule is also conceivable (see also FIGS. 10A through 10D and 11A through 11D); in this case, the capsule is clamped into a suitable dispensing device, for example, and emptied by applying pressure to at least one combination of piston/piston body that can be moved inside the capsule body.

In the event that more than three components are needed, whereby two of them may be jointly present in the mixing chamber, in the absence of the other components, the mixing chamber may be charged in particular with solids or with stuffable dental composites containing the reactive components. This means it is not possible for said components to be mixed before pistons 3 are activated, after which all the components can subsequently be mixed.

Figure 4:
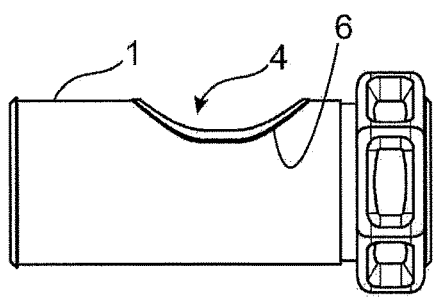
FIG. 4A shows a front side view of the capsule body of the mixing capsule according to the first embodiment.
FIG. 4B show the right side view of the capsule body of the mixing capsule according to the first embodiment.
FIG. 4C shows top side view of the capsule body of the mixing capsule according to the first embodiment.
FIG. 4D shows a cross-section view of sectional plane IV of FIG. 4C.
Figure 4:
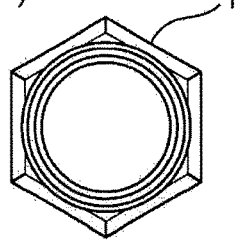
Figure 4:
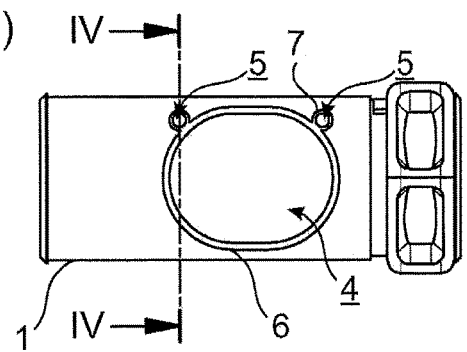
Figure 4:
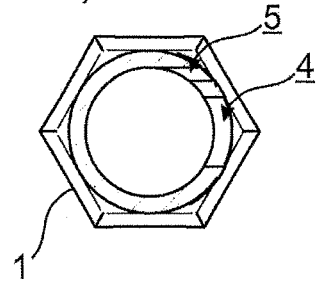

FIGS. 4A, through 4D show views and sectional planes of a capsule body 1 of mixing capsule 22 according to the first embodiment.

FIGS. 4A, 4B and 4C show different views of capsule body 1, with FIG. 4D showing a cross-section indicated by sectional plane IV in FIG. 4C. Capsule body 1 has an outlet opening 4, which is encircled by a seal 6. Near the edge of outlet opening 4, there are two vent holes 5 each provided with their own seal 7.

FIGS. 5A and 5B show perspective views of capsule body 1 of mixing capsule 22 according to the first embodiment.

The details of the capsule body, namely outlet opening 4, vent holes 5 and seals 6 and 7, as already shown in FIGS. 4A through 4D, can also be seen in FIGS. 5A and 5B.

The view in FIG. 5B also shows stop member 8, which interacts with a recess 11 in the sleeve in order to limit the relative movement (or more precisely the rotation) between capsule body 1 and sleeve 10 (see below).

FIGS. 6A and 6B show perspective grid views of a sleeve 10 of mixing capsule 22 according to the first embodiment.

Like capsule body 1 as well (see above), the sleeve has a substantially cylindrical shape, the inner diameter of sleeve 10 being selected such that, in combination with capsule body 1, sleeve 10 can act as a seal.

Sleeve 10 has a sleeve opening 13, the size and shape of which are substantially identical to the size and shape of outlet opening 4 of capsule body 1.

In regions whose position is based on the position of vent holes 5 of the capsule body, the wall of sleeve 10 is configured in such a way that there is a flat recess, with the result that ventilation passages 12 are formed. Collar 9 of sleeve 10 is provided with a recess 11 for receiving stop member 8 and which interacts with the latter to limit relative rotation of capsule body 1 and sleeve 10.

FIGS. 7A through 7E shows views and cross-sections of the sleeves of mixing capsule 22 according to the first embodiment.

Figure 7A:
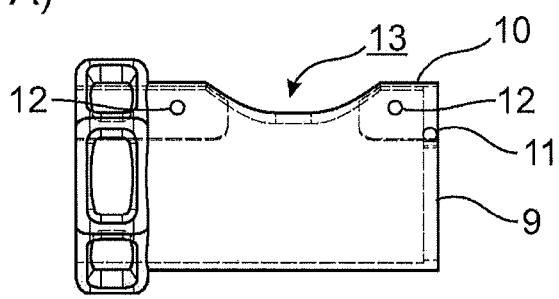
FIG. 7A shows front side view of the internal structure of the sleeve of the mixing capsule according to the first embodiment.
Figure 7B:
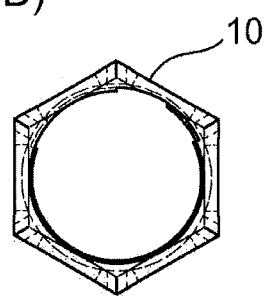
FIG. 7B shows cross-section of the internal structure of the sleeve of mixing capsule according to the first embodiment.
Figure 7C:
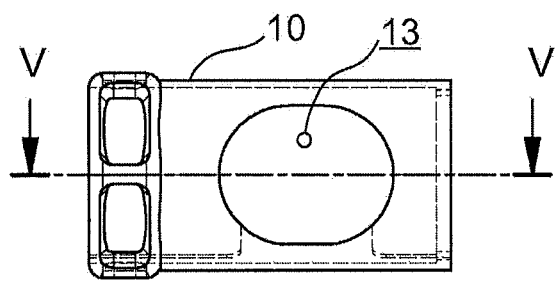
FIG. 7C shows top view of the internal structure of the sleeve of the mixing capsule according to the first embodiment.

FIGS. 7A through 7C indicate with broken lines the internal structure of sleeve 10, which could not be seen otherwise due to its outer wall.

Figure 7D:
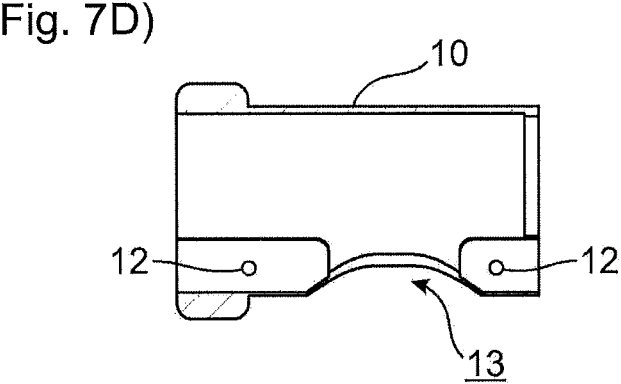
FIG. 7D shows a cross-sectional view along sectional plane V as indicated in FIG. 7C.

FIG. 7D shows a cross-sectional view along sectional plane V as indicated in FIG. 7C.

Part of sleeve opening 13 can be seen in FIG. 7D, where the wall of sleeve 10 is provided with a recess adjacent to sleeve opening 13, with the result that a ventilation passage 12 is provided in the region where the material is thus recessed.

Figure 7E:
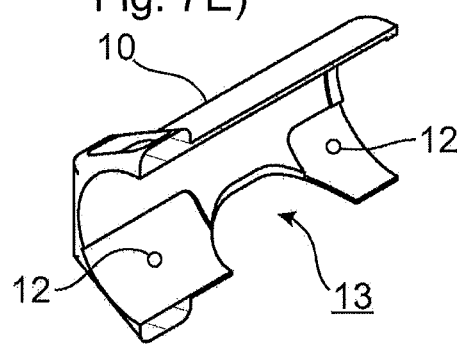
FIG. 7E show a perspective view of the cross-section shown in FIG. 7D.
Figure 8A:
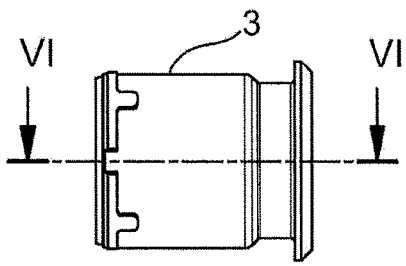
FIG. 8A shows a front side view of the piston of the mixing capsule according to the first embodiment.
Figure 8B:
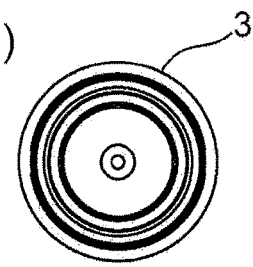
FIG. 8B shows a right side view of the piston of the mixing capsule according to the first embodiment.
Figure 8C:
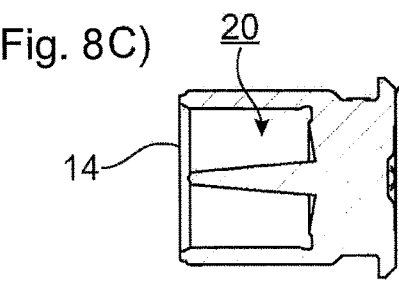
FIG. 8C shows a cross sectional view along the sectional plane VI as indicated in FIG. 8A.
Figure 8D:
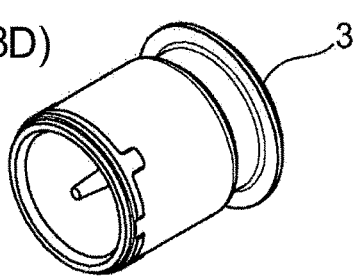
FIG. 8D shows a perspective view of the piston of the mixing capsule according to the first embodiment.
Figure 9A:
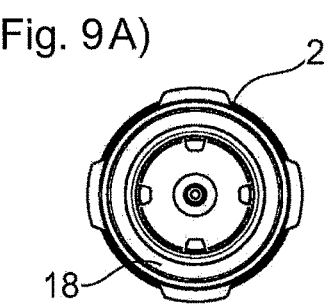
FIG. 9A shows a left side view of the piston of the mixing capsule according to the first embodiment.
Figure 9B:
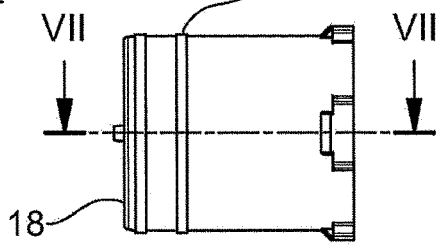
FIG. 9B shows a front side view of the piston of the mixing capsule according to the first embodiment.
Figure 9C:
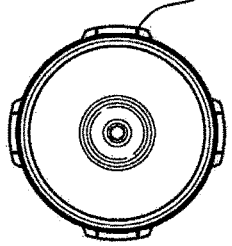
FIG. 9C shows a right side view of the piston of the mixing capsule according to the first embodiment.
Figure 9D:
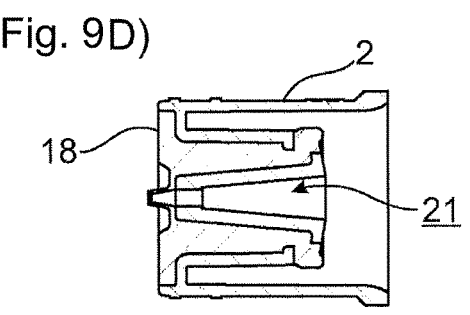
FIG. 9D shows a cross sectional view along the sectional plane VII as indicated in FIG. 9B of the piston body of the mixing capsule according to the first embodiment.
Figure 9E:
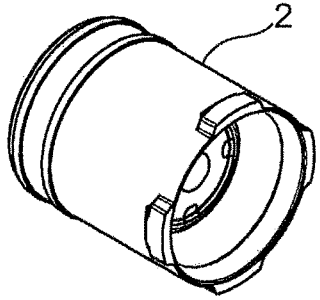
FIG. 9E shows a perspective view of the piston of the mixing capsule according to the first embodiment.

FIG. 7E is a perspective view of the cross-section shown in FIG. 7D.

FIGS. 8B through 8D and 9A through 9B show views and cross-sections of a piston 3 of mixing capsule 22 according to the first embodiment, and a piston body 2 of mixing capsule 22 according to the first embodiment.

For details of piston bodies 2 and pistons 3, reference is made here to the content of European patent application EP 2 510 897 A2, the disclosure of which is incorporated here by reference, insofar as it relates to details of piston body 2 and piston 3.

Figure 10:
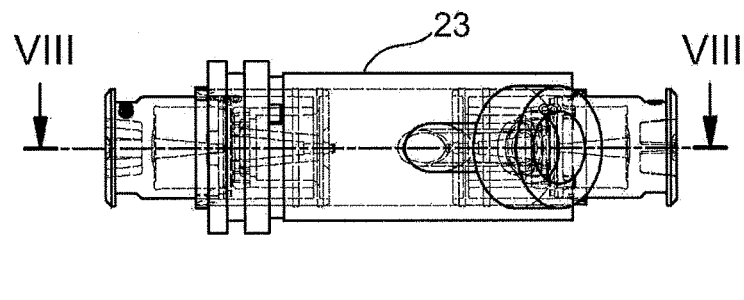
FIG. 10A shows an internal view of the mixing capsule according to a second embodiment of the invention.
FIG. 10B shows a cross section view of the mixing capsule according to a second embodiment of the invention.
FIG. 10C shows an internal view of the mixing capsule with the second embodiment extended.
FIG. 10D shows a cross section view of the mixing capsule with the second embodiment extended.
Figure 10:
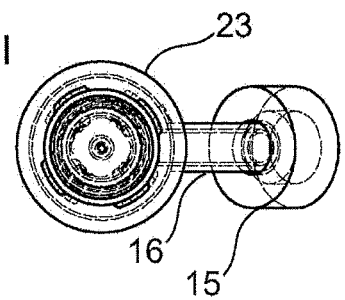
Figure 10:
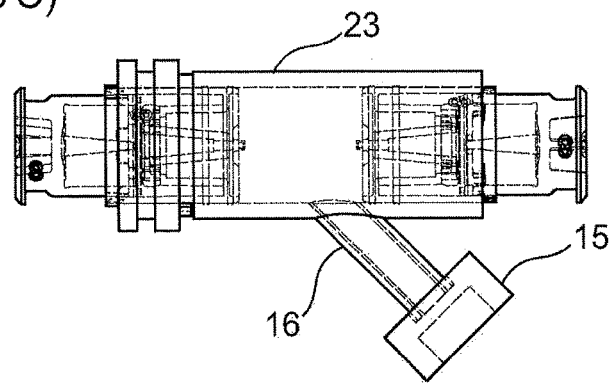
Figure 10:
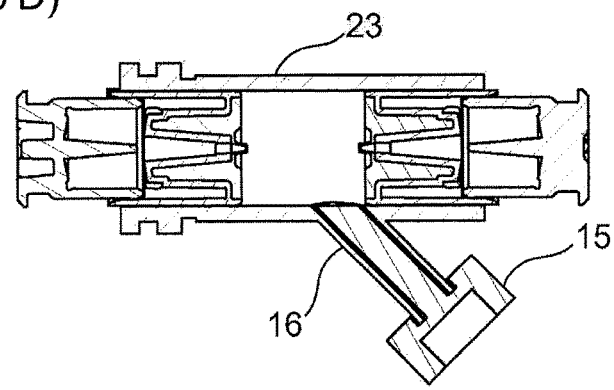

FIGS. 10A through 10B show views and a cross-section of a mixing capsule 23 according to a second embodiment of the invention.

As in the first embodiment, there is a substantially cylindrical capsule body into which piston bodies and pistons are inserted.

Unlike the first embodiment, however, this embodiment does not have a sleeve. Instead, the outlet opening of the mixing chamber is formed by an application cannula 16, which is closed by means of a closure means 15 so that, until closure means 15 is removed, the mixing chamber is hermetically closed by the capsule body and the piston bodies, at least to the extent that no undesired external influences can reach the mixing chamber. As in the first embodiment also, vent holes (not shown) may be provided in order to release any gases that are produced during mixing and possible reaction of the mixing components.

FIGS. 11A through 11D shows views and a cross-section of a mixing capsule 24 according to a third embodiment of the invention. In contrast to the first and the second embodiment, the two piston bodies (and hence also the pistons) are not arranged here along the longitudinal axis of mixing capsule 24. In this case, only one of the piston bodies is in a position in which it is arranged along the longitudinal axis of mixing capsule 24, and on the opposite side of the capsule body from this piston body an application cannula 16 is moulded which defines the outlet opening of the mixing chamber in the capsule body and which is closed by means of a closure means 17. Here, the second piston body is inserted into a projecting collar formed on a side wall of the capsule body and likewise ends at the mixing chamber.

FIG. 12A through 12E show views of a mixing capsule 25 according to a fourth embodiment of the invention, in an initial state. As regards its structure, mixing capsule 25 according to the fourth embodiment is largely identical to mixing capsule 23 according to the second embodiment and as shown in FIGS. 10A through 10D.

Unlike the second embodiment, application cannula 16, which can be closed by closure means 15, is provided in such a way that it extents substantially at right angles to capsule body 1.

Another difference from mixing capsule 23 according to the second embodiment is that mixing capsule 25 is provided with a piston body 2' which is selectively blocked or released for longitudinal displacement inside capsule body 1 in the direction of the opposite piston body 2. When released for longitudinal displacement, piston body 2' can be pressed in the direction of the opposite piston body 2, with the result that mixing chamber 19, which is delimited by capsule body 1 and by piston bodies 2, 2', is reduced in size in such a way that any (mixed) dental preparation (not shown) that may be mixing chamber 19 is driven out through application cannula 16.

Piston body 2', which already extends partially inside capsule body 1, in the initial state shown in FIGS. 12A through 12E, is provided with a projecting arm 26 which abuts against a shoulder 27 of capsule body 1, such that when arm 26 abut against shoulder 27, any further pressing of piston body 2' into capsule body 1 is prevented. In such a state, a force can be exerted in the longitudinal direction of mixing capsule 25 on piston 3 in piston body 2' in order to press piston 3 into piston body 2', without piston 3 being able to escape from that force by displacement of piston body 2'.

In another variant, any escape from said force can also be prevented by suitably adjusting the forces needed to displace piston 3 in piston body 2', and to displace piston body 2' in capsule body 1.

However, one advantage of selectively blocking any relative displacement of piston body 2' inside capsule body 1 by constructional design is that the transition from pressing piston 3 into piston body 2', on the one hand, to pressing piston body 2' into capsule body 1, on the other, can be effected in a more defined manner.

Shoulder 27 is provided with a ramp 28 which forms a transition from one plane of the outer wall of piston body 2' (contacting an inner wall of capsule body 1) to the outer wall of capsule body 1. When piston body 2' and capsule body 1 are turned relative to each other, arm 26 and ramp 28 can be positioned to match each other, so that arm 26 is no longer blocked by shoulder 27 from displacement in the longitudinal direction and instead is guided by ramp 28 onto the outer wall of capsule body 1 when displaced.

As an alternative or in addition thereto, the arm (or some other element corresponding thereto) can also be provided as a removable part (e.g. with a predetermined breaking point). If, for example, two arms (of which one is removable) are provided in conjunction with only one ramp, then the piston body can only be inserted further into the capsule body, in the event that the piston body and the capsule body are inadvertently turned relative to each other, if the removable arm is removed and the remaining arm and the ramp are matchingly positioned.

Figure 13:
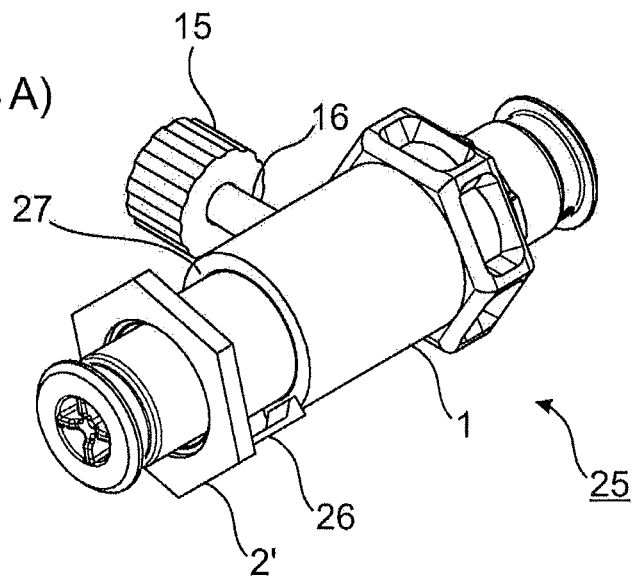
FIG. 13A shows a perspective view of the mixing capsule according to the fourth embodiment in an initial state.
FIG. 13B shows a perspective view of the mixing capsule according to the fourth embodiment in a state after the mixed dental material has been expelled.
Figure 13:
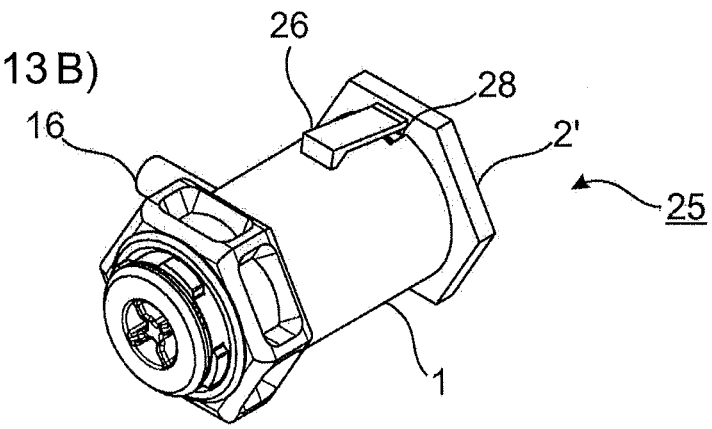

FIGS. 13A and 13B show views of mixing capsule 25 according to the fourth embodiment, in an initial state and in a state after the mixed dental material has been expelled.

This view of the initial state corresponds to the views shown in FIGS. 12A through 12B from a different angle of vision. In the view of the state after expulsion of the mixed dental material, it can be seen that arm 26 now extends over the outer wall of capsule body 1 after being guided by ramp 28.

It is also possible that, instead of ramp 28, a groove (not shown) be provided in the outer wall of the capsule body, into which the arm can enter.

FIGS. 14A through 14E partly show views and partly show cross-sections of mixing capsule 25 according to the fourth embodiment, illustrating step by step how the mixing capsule is used.

Figure 14A:
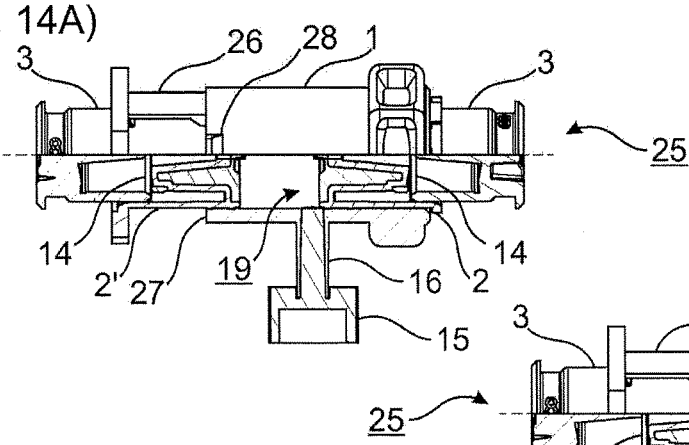
FIG. 14A shows a side view and cross-sectional view of the mixing capsule according to the fourth embodiment in its initial state in which the piston is inserted only a little into the piston body and the fluids (not shown) accommodated in the piston is tightly sealed by a respective film.

FIG. 14A shows the initial state in which pistons 3 are inserted only a little into piston bodies 2, 2', and the fluids (not shown) accommodated in pistons 3 are tightly sealed into pistons 3 by a respective film 14.

Figure 14B:
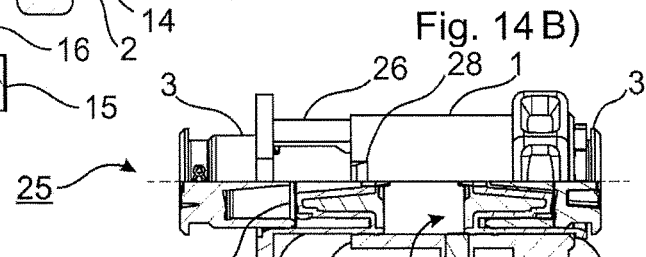
FIG. 14B shows a side view and cross-sectional view of the mixing capsule according to the fourth embodiment transitioning in which the piston has been inserted into the piston body, and after the film has been ruptured, the fluid has been pressed as a result into mixing chamber, where it comes into contact with a mixing component (not shown).

Transitioning to FIG. 14B, piston 3 has been inserted into piston body 2, and after film 14 has been ruptured, the fluid has been pressed as a result into mixing chamber 19, where it comes into contact with a mixing component (not shown).

Figure 14C:
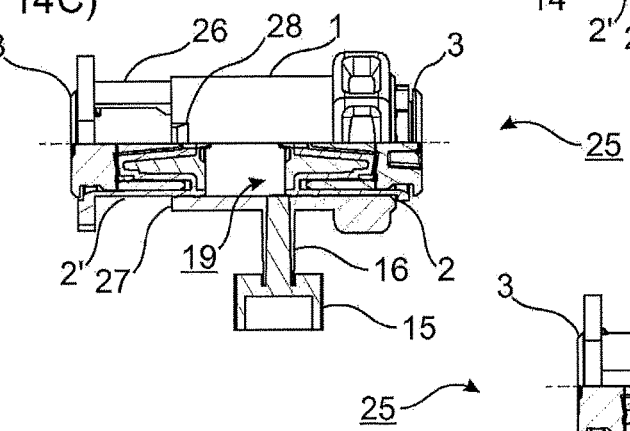
FIG. 14C shows a side view and cross-sectional view of the mixing capsule according to the fourth embodiment transitioning in which the piston has also been inserted into piston body, with the result that the fluid contained in the piston reaches mixing chamber dass after destruction of film 14.

Transitioning to FIG. 14C, piston 3 has also been inserted into piston body 2', with the result, here as well, that the fluid contained in piston 3 reaches mixing chamber 19 dass after destruction of film 14.

The separate views in FIGS. 14B and 14C are shown for illustrative purposes, and it is possible to reverse the order. The fluids contained in pistons 3 can also be introduced substantially simultaneously into mixing chamber 19.

Figure 14D:
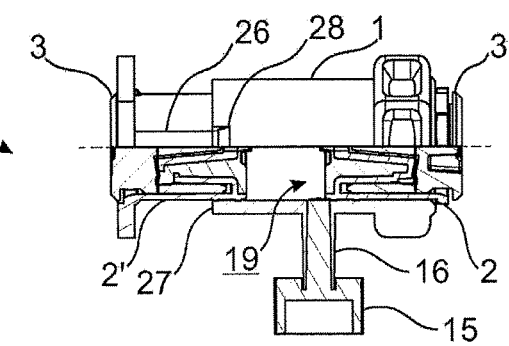
FIG. 14D shows a side view and cross-sectional view of the mixing capsule according to the fourth embodiment transitioning in which piston body has been turned relative to capsule body in such a way that the arm is aligned with the ramp. the mixing capsule is ready for piston body to be inserted into capsule body.

It can be seen from a comparison of FIG. 14C and FIG. 14D that FIG. 14D shows a state in which piston body 2' has been turned relative to capsule body 1 in such a way that arm 26 is aligned with ramp 28. In contrast to FIG. 14D, FIGS. 14A through 14C show states in which arm 26 abuts a shoulder 27 or the end of capsule body 1. In the state shown in FIG. 14D, the mixing capsule is ready for piston body 2' to be inserted into capsule body 1.

Figure 14E:
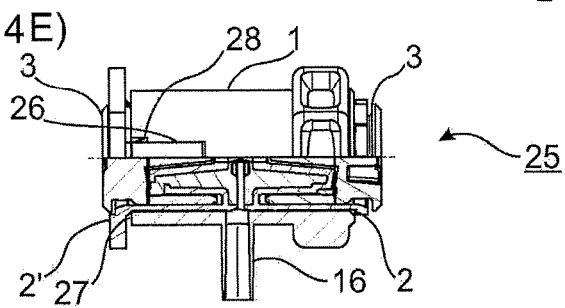
FIG. 14E shows a side view and cross-sectional view of the mixing capsule according to the fourth embodiment transitioning in which the piston body has been fully inserted into capsule body, with mixed dental preparation (not shown) having been expelled from the mixing chamber through application cannula on insertion.

FIG. 14E shows a state in which piston body 2' has been fully inserted into capsule body 1, with mixed dental preparation (not shown) having been expelled from mixing chamber 19 through application cannula 16 on insertion. Piston bodies 2, 2' now abut each other, theoretically, with the result that mixing chamber 19 has theoretically been reduced to zero. In practice, it is possible that complete emptying is not achieved.

It is possible that all the piston bodies of the mixing capsule are designed to be displaceable similarly to piston body 2'. If, for example, three piston body/piston combinations are provided, two of which are opposite each other, then these two piston bodies may be configured in such a way that they define a residual space (a mixing chamber of reduced size) in the inserted or pressed-in state, the cross-section of which matches that of the third piston body, so that the remaining dental preparation can then be expelled through an outlet opening by pressing the third piston bodies into the latter cross-section, said outlet opening being opposite the third piston body, for example.

As already noted above, mixing capsule 25 according to the fourth embodiment is similar in some respects to mixing capsule 23 according to the second embodiment. Unlike in the latter, however, piston body 2' and capsule body 1 are designed to be displaceable here. After mixing and before expulsion, piston body 2' and capsule body 1 are still advantageously locked, and their displaceability is not released until they are turned (in other embodiments, some other measure may also be provided). Due to the pressure in the longitudinal direction, material is then conveyed through the trunk, as an example of an application cannula. The displaceable length is preferably the same here as the length of mixing chamber 19.

This embodiment makes it easier for the use to remove the material, without an additional removal device being needed.

The present invention allows a homogenously mixed dental material to be provided, consisting of liquid and/or pasty and/or stuffable and/or solid components that are spatially separated from each other in a mixing capsule.

The mixing capsule according to the invention allows three and more components to be stored and mixed in just one system. By simple activation and with a brief mixing operation, it is thus possible to provide a dental material having above-average material properties, in that otherwise incompatible components are spatially separated yet nevertheless combined in one system. The possibility of using two components A1 and A2 of different viscosities is particularly helpful in this regard. This has advantageous effects on the mixing result, and allows highly versatile combinations of components C1-Cn, whose viscosity can thus be selected from an almost unlimited range.

In one embodiment, the invention provides a mixing capsule for producing a dental preparation, said mixing capsule comprising a capsule body having a mixing chamber for receiving a mixing component and for mixing the dental preparation from the mixing component, a first fluid and a second fluid and having an outlet opening for expelling the dental preparation, a first cavity for receiving the first fluid, a first passageway for guiding the first fluid, a second cavity for receiving a second fluid, a second passageway for guiding the second fluid, the two cavities being displaceable relative to the mixing chamber, as a result of which both fluids can be guided through the passageways assigned to them and into the mixing chamber, where they can be mixed with each other.

To activate, a force can be exerted on the first cavity, thus causing a relative displacement of the first cavity relative to the mixing chamber, as a result of which the mixing chamber may be reduced in size by said displacement.

To activate, a force causing a relative displacement of the first cavity relative to the mixing chamber can be exerted on the first cavity, the direction and amount of the force being appropriate to also cause a relative displacement of the second cavity relative to the mixing chamber.

The respective passageway preferably has a closure means at the mixing chamber end, wherein said closure means opens the path into the mixing chamber by the action of fluid pressure.

More particularly, the mixing chamber may contain a third component which can mix with the first and with the second component.

The length of the capsule during mixing is preferably less than 40 mm.

It is further preferred if the mixing chamber has provisions for relieving pressure (of compressed gas), which prevent liquid or paste from squirting out when the mixing chamber is opened.

LIST OF REFERENCE SIGNS

1 Capsule body
2, 2' Piston body
3 Piston
4 Outlet opening
5 Vent hole
6 Seal

7 Seal
8 Stop member
9 Collar
10 Sleeve
11 Recess
12 Ventilation passage
13 Sleeve opening
14 Film
15 Closure
16 Application cannula
17 Closure means
18 Side of the piston body facing the mixing chamber
19 Mixing chamber
20 Cavity
21 Passageway
22, 23, 24, 25 Mixing capsule
26 Arm
27 Shoulder
28 Ramp

The invention claimed is:

1. A mixing capsule (22, 23, 24, 25) for producing a dental preparation, said mixing capsule (22, 23, 24, 25) comprising:
a capsule body (1) having a mixing chamber (19) for receiving a mixing component and for mixing the dental preparation from the mixing component, a first fluid and a second fluid and having an outlet opening (4) in fluid communication with the mixing chamber for expelling the dental preparation,
a first cavity (20) for receiving the first fluid,
a first piston body (2, 2') defining the mixing chamber (19) in the capsule body (1) and having a first passageway (21) for guiding the first fluid from the first cavity (20) into the mixing chamber (19),
a second cavity (20) for receiving the second fluid and
a second piston body (2, 2') defining the mixing chamber (19) in the capsule body (1) and having a second passageway (21) for guiding the second fluid from the second cavity (20) into the mixing chamber (19).

2. The mixing capsule (22) according to claim 1,
said mixing capsule (22) having a sleeve (10) which encloses the capsule body (1) at least partially and which is to be disposed in at least a first and a second position relative to the capsule body (1),
wherein the sleeve (10) closes the outlet opening (4) in the first position and exposes the outlet opening (4) in the second position, so that the dental preparation can be expelled through the outlet opening (4).

3. The mixing capsule (22) according to claim 2,
wherein the sleeve (10) has an opening (13) and the sleeve opening (13) and the outlet opening (4) can be brought into alignment with each other in the second position by turning and/or sliding the sleeve (10) and the capsule body (1) relative to each other, so that the dental preparation can be expelled through the outlet opening (4) and the sleeve opening (13), and can be separated from each other in the first position so that the sleeve (10) closes the outlet opening (4).

4. The mixing capsule (22) according to claim 3,
wherein the capsule body (1) has a cylindrical outer shape in at least one portion thereof,
the outlet opening (4) being located in said portion,
wherein the sleeve (10) encloses the capsule body (1) at least partially in at least a part of said portion and is configured so that the sleeve (10) and the capsule body (1) can be turned relative to each other.

5. The mixing capsule (22) according to claim 3,
wherein the sleeve opening (13) leads to an application means for the sleeve (10), in particular to a cannula.

6. The mixing capsule (22) according to claim 2,
wherein the first piston body (2, 2') is adapted to close the outlet opening (4),
wherein the sleeve (10) is separated in the second position from the capsule body (1) and
wherein the sleeve (10) is adapted to entrain the first piston body (2, 2') in order to expose the outlet opening (4) on separation of the sleeve (10) from the capsule body (1).

7. The mixing capsule (22) according to claim 2,
wherein the piston body (2, 2') and/or the sleeve (10) have one or more detent means for snap-locking the piston body (2, 2') and the sleeve (10) together in the first, the second and/or in a third position.

8. The mixing capsule (22, 23, 24, 25) according to claim 1,
wherein the first and the second piston body (2, 2') are arranged opposite one another and the mixing chamber (19) is located between the first and the second piston body (2, 2').

9. The mixing capsule (25) according to claim 1,
wherein the first piston body (2, 2') and/or the second piston body (2, 2') are displaceable inside the capsule body (1).

10. The mixing capsule (25) according to claim 1,
wherein the first piston body (2, 2') can be displaced up to a maximum depth of penetration into the capsule body (1),
wherein the first piston body (2, 2') adjoins the outlet opening (4) at its maximum depth of penetration.

11. The mixing capsule (22, 23, 24, 25) according to claim 1, wherein the outlet opening (4) is in fluid communication with the first and/or the second piston body and is closed by a removable closure means.

12. The mixing capsule (22, 23, 24, 25) according to claim 1,
said mixing capsule (22, 23, 24, 25) having a sleeve (10) which encloses the capsule body (1) at least partially and which is to be disposed in at least a third and a fourth position relative to the capsule body (1),
wherein the sleeve (10) has a cavity for receiving an admixing component,
wherein the sleeve (10) is arranged in the third position in such a way that the cavity is in communication with the mixing chamber (19) so that admixing components can enter the mixing chamber (19), and the sleeve is arranged in the fourth position in such a way that the cavity is shut off from the mixing chamber (19) and from surroundings of the mixing capsule (22, 23, 24, 25).

* * * * *